(12) United States Patent
Vansickle et al.

(10) Patent No.: US 11,565,131 B2
(45) Date of Patent: Jan. 31, 2023

(54) OPTICAL STIMULATION SYSTEMS WITH CALIBRATION AND METHODS OF MAKING AND USING

(71) Applicants: Boston Scientific Neuromodulation Corporation, Valencia, CA (US); COMMISSARIAT A L'ENERGIE ATOMIQUE ET AUX ENERGIES ALTERNATIVES ("CEA"), Paris (FR)

(72) Inventors: Dennis Allen Vansickle, Lancaster, CA (US); Adam Thomas Featherstone, Meridian, ID (US); Claude Chabrol, Poisat (FR); Michael A. Moffitt, Solon, OH (US); Sarah Renault, Corenc (FR); Adrien Poizat, Voiron (FR)

(73) Assignees: BOSTON SCIENTIFIC NEUROMODULATION CORPORATION, Valencia, CA (US); COMMISSARIAT A L'ENERGIE ATOMIQUE ET AUX ENERGIES ALTERNATIVES ("CEA"), Paris (FR)

( * ) Notice: Subject to any disclaimer, the term of this patent is extended or adjusted under 35 U.S.C. 154(b) by 0 days.

(21) Appl. No.: 17/040,233

(22) PCT Filed: Mar. 19, 2019

(86) PCT No.: PCT/US2019/022917
§ 371 (c)(1),
(2) Date: Sep. 22, 2020

(87) PCT Pub. No.: WO2019/183054
PCT Pub. Date: Sep. 26, 2019

(65) Prior Publication Data
US 2021/0016111 A1    Jan. 21, 2021

Related U.S. Application Data

(60) Provisional application No. 62/647,561, filed on Mar. 23, 2018.

(51) Int. Cl.
A61N 5/10        (2006.01)
A61N 5/06        (2006.01)

(52) U.S. Cl.
CPC ......... *A61N 5/1075* (2013.01); *A61N 5/0601* (2013.01); *A61N 5/0622* (2013.01); *A61N 2005/063* (2013.01)

(58) Field of Classification Search
CPC .. A61N 5/1075; A61N 5/0601; A61N 5/0622; A61N 2005/063; A61N 2005/0626
See application file for complete search history.

(56) References Cited

U.S. PATENT DOCUMENTS

| 4,920,979 A | 5/1990 | Bullara |
| 5,076,270 A | 12/1991 | Stutz, Jr. |

(Continued)

FOREIGN PATENT DOCUMENTS

| WO | 02/091935 | 11/2002 |
| WO | 2011/031131 | 3/2011 |

(Continued)

OTHER PUBLICATIONS

Baxter, G.D. et al., Effects of Low Intensity Infrared Laser Irradiation Upon Conduction in the Human Median Nerve In Vivo, Experimental Physiology (1994) 79, 227-234.

(Continued)

*Primary Examiner* — Brian T Gedeon
*Assistant Examiner* — Joshua Andrew Schum-Houck
(74) *Attorney, Agent, or Firm* — Branch Partners PLLC; Bruce E. Black

(57) ABSTRACT

An optical stimulation system includes a light source; an optical lead coupled, or coupleable, to the light source; at least one of a calibration table or a calibration formula, generated by a calibration procedure specifically using the light source and the optical lead of the optical stimulation (Continued)

system; and a control unit coupled, or coupleable, to the light source. The control module includes a memory to store the at least one of the calibration table or the calibration formula, and a processor coupled to the memory and configured for receiving a target light output level, using the at least one of the calibration table or the calibration formula to determine at least one operational parameter for generating the target light output level, and directing the light source, using the at least one operational parameter, to generate light at the target light output level.

20 Claims, 8 Drawing Sheets

(56) References Cited

U.S. PATENT DOCUMENTS

| | | | |
|---|---|---|---|
| 5,437,193 A | 8/1995 | Schleitweiler et al. |
| 5,445,608 A | 8/1995 | Chen et al. |
| 5,556,421 A | 9/1996 | Prutchi et al. |
| 5,824,027 A | 10/1998 | Hoffer et al. |
| 6,175,710 B1 | 1/2001 | Kamaji et al. |
| 6,181,969 B1 | 1/2001 | Gord |
| 6,224,450 B1 | 5/2001 | Norton |
| 6,271,094 B1 | 8/2001 | Boyd et al. |
| 6,295,944 B1 | 10/2001 | Lovett |
| 6,364,278 B1 | 4/2002 | Lin et al. |
| 6,366,719 B1 | 4/2002 | Heath et al. |
| 6,391,985 B1 | 5/2002 | Goode et al. |
| 6,442,435 B2 | 8/2002 | King et al. |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 6,895,280 B2 | 5/2005 | Meadows et al. |
| 6,988,001 B2 | 1/2006 | Greatbatch et al. |
| 6,993,384 B2 | 1/2006 | Bradley et al. |
| 7,190,993 B2 | 3/2007 | Sharma et al. |
| 7,244,150 B1 | 7/2007 | Brase et al. |
| 7,252,677 B2 | 8/2007 | Burwell et al. |
| 7,288,108 B2 | 10/2007 | DiMauro et al. |
| 7,395,118 B2 | 7/2008 | Erickson |
| 7,437,193 B2 | 10/2008 | Parramon et al. |
| 7,450,997 B1 | 11/2008 | Pianca et al. |
| 7,672,734 B2 | 3/2010 | Anderson et al. |
| 7,684,869 B2 | 3/2010 | Bradley et al. |
| 7,736,382 B2 | 6/2010 | Webb et al. |
| 7,761,165 B1 | 7/2010 | He et al. |
| 7,783,359 B2 | 8/2010 | Meadows |
| 7,792,590 B1 | 9/2010 | Pianca et al. |
| 7,803,021 B1 | 9/2010 | Brase |
| 7,809,446 B2 | 10/2010 | Meadows |
| 7,946,980 B2 | 5/2011 | Reddy et al. |
| 7,949,395 B2 | 5/2011 | Kuzma |
| 7,949,409 B2 | 5/2011 | Bly et al. |
| 7,974,706 B2 | 7/2011 | Moffitt et al. |
| 8,086,322 B2 | 12/2011 | Schouenborg |
| 8,175,710 B2 | 5/2012 | He |
| 8,224,450 B2 | 7/2012 | Brase |
| 8,271,094 B1 | 9/2012 | Moffitt et al. |
| 8,295,944 B2 | 10/2012 | Howard et al. |
| 8,311,647 B2 | 11/2012 | Bly |
| 8,326,433 B2 | 12/2012 | Blum et al. |
| 8,340,785 B2 | 12/2012 | Bonde et al. |
| 8,364,278 B2 | 1/2013 | Pianca et al. |
| 8,386,054 B2 | 2/2013 | North |
| 8,391,985 B2 | 3/2013 | McDonald |
| 8,463,343 B2 | 6/2013 | Kuhn et al. |
| 8,473,061 B2 | 6/2013 | Moffitt et al. |
| 8,483,237 B2 | 7/2013 | Zimmermann et al. |
| 8,525,027 B2 | 9/2013 | Lindner et al. |
| 8,571,665 B2 | 10/2013 | Moffitt et al. |
| 8,600,509 B2 | 12/2013 | McDonald et al. |
| 8,675,945 B2 | 3/2014 | Barnhorst et al. |
| 8,682,439 B2 | 3/2014 | DeRohan et al. |
| 8,688,235 B1 | 4/2014 | Pianca et al. |
| 8,792,993 B2 | 7/2014 | Pianca et al. |
| 8,831,731 B2 | 9/2014 | Blum et al. |
| 8,831,742 B2 | 9/2014 | Pianca et al. |
| 8,831,746 B2 | 9/2014 | Swanson |
| 8,849,632 B2 | 9/2014 | Sparks et al. |
| 8,868,211 B2 | 10/2014 | Durand et al. |
| 8,897,876 B2 | 11/2014 | Sundaramurthy et al. |
| 8,929,973 B1 | 1/2015 | Webb et al. |
| 8,936,630 B2 | 1/2015 | Denison et al. |
| 8,958,615 B2 | 2/2015 | Blum et al. |
| 9,238,132 B2 | 1/2016 | Barker |
| 9,409,032 B2 | 8/2016 | Brase et al. |
| 9,415,154 B2 | 8/2016 | Leven |
| 9,421,362 B2 | 8/2016 | Seeley |
| 9,440,066 B2 | 9/2016 | Black |
| 9,550,063 B2 | 1/2017 | Wolf, II |
| 9,604,068 B2 | 3/2017 | Malinowski |
| 9,643,010 B2 | 5/2017 | Ranu |
| 9,656,093 B2 | 5/2017 | Villarta et al. |
| 9,681,809 B2 | 6/2017 | Sharma et al. |
| 9,770,598 B2 | 9/2017 | Malinowski et al. |
| 9,931,511 B2 | 4/2018 | Kaula et al. |
| 10,307,602 B2 | 6/2019 | Leven |
| 10,471,273 B2 | 11/2019 | Segev et al. |
| 2002/0156513 A1 | 10/2002 | Borkan |
| 2002/0161417 A1 | 10/2002 | Scribner |
| 2004/0098063 A1 | 5/2004 | Goetz |
| 2004/0147964 A1 | 7/2004 | Nolan et al. |
| 2005/0216072 A1 | 9/2005 | Mahadevan-Jansen et al. |
| 2006/0129210 A1 | 6/2006 | Cantin et al. |
| 2006/0155348 A1 | 7/2006 | deCharms |
| 2006/0161227 A1 | 7/2006 | Walsh et al. |
| 2007/0053996 A1 | 3/2007 | Boyden et al. |
| 2007/0100398 A1 | 5/2007 | Sloan |
| 2007/0150036 A1 | 6/2007 | Anderson |
| 2007/0161919 A1 | 7/2007 | DiLorenzo |
| 2007/0244526 A1 | 10/2007 | Zaghetto et al. |
| 2008/0046053 A1 | 2/2008 | Wagner et al. |
| 2008/0077198 A1 | 3/2008 | Webb et al. |
| 2008/0146890 A1 | 6/2008 | LeBoeuf et al. |
| 2008/0167701 A1 | 7/2008 | John et al. |
| 2008/0197300 A1 | 8/2008 | Kayser et al. |
| 2008/0243218 A1 | 10/2008 | Bottomley et al. |
| 2009/0054954 A1 | 2/2009 | Foley et al. |
| 2009/0054955 A1* | 2/2009 | Kopell ............... A61N 5/0601 607/88 |
| 2009/0069871 A1 | 3/2009 | Mahadevan-Jansen et al. |
| 2009/0118800 A1 | 5/2009 | Deisseroth et al. |
| 2009/0187222 A1 | 7/2009 | Barker |
| 2009/0196471 A1 | 8/2009 | Goetz et al. |
| 2009/0276021 A1 | 11/2009 | Meadows et al. |
| 2009/0287272 A1 | 11/2009 | Kokones et al. |
| 2009/0287273 A1 | 11/2009 | Carlton et al. |
| 2010/0076508 A1 | 3/2010 | McDonald et al. |
| 2010/0076535 A1 | 3/2010 | Pianca et al. |
| 2010/0094364 A1 | 4/2010 | McDonald |
| 2010/0105997 A1 | 4/2010 | Ecker et al. |
| 2010/0114190 A1 | 5/2010 | Bendett et al. |
| 2010/0174329 A1 | 7/2010 | Dadd et al. |
| 2010/0174344 A1 | 7/2010 | Dadd et al. |
| 2010/0256693 A1 | 10/2010 | McDonald et al. |
| 2010/0268298 A1 | 10/2010 | Moffitt et al. |
| 2010/0292758 A1 | 11/2010 | Lee et al. |
| 2010/0324630 A1 | 12/2010 | Lee et al. |
| 2010/0326701 A1 | 12/2010 | McDonald |
| 2011/0004267 A1 | 1/2011 | Meadows |
| 2011/0005069 A1 | 1/2011 | Pianca |
| 2011/0009932 A1 | 1/2011 | McDonald et al. |
| 2011/0022100 A1 | 1/2011 | Brase et al. |
| 2011/0029055 A1 | 2/2011 | Tidemand |
| 2011/0046432 A1 | 2/2011 | Simon et al. |
| 2011/0046700 A1 | 2/2011 | McDonald et al. |
| 2011/0078900 A1 | 4/2011 | Pianca et al. |
| 2011/0106208 A1 | 5/2011 | Faltys et al. |
| 2011/0112591 A1 | 5/2011 | Seymour et al. |
| 2011/0125077 A1 | 5/2011 | Denison et al. |
| 2011/0125078 A1 | 5/2011 | Denison et al. |

(56) References Cited

U.S. PATENT DOCUMENTS

| | | |
|---|---|---|
| 2011/0130803 A1 | 6/2011 | McDonald |
| 2011/0130816 A1 | 6/2011 | Howard et al. |
| 2011/0130817 A1 | 6/2011 | Chen |
| 2011/0130818 A1 | 6/2011 | Chen |
| 2011/0172653 A1 | 7/2011 | Schneider et al. |
| 2011/0172725 A1 | 7/2011 | Wells et al. |
| 2011/0238129 A1 | 9/2011 | Moffitt et al. |
| 2011/0295331 A1 | 12/2011 | Wells et al. |
| 2011/0313500 A1 | 12/2011 | Barker et al. |
| 2012/0014580 A1 | 1/2012 | Blum et al. |
| 2012/0016378 A1 | 1/2012 | Pianca et al. |
| 2012/0046710 A1 | 2/2012 | Digiore et al. |
| 2012/0046715 A1 | 2/2012 | Moffitt et al. |
| 2012/0071949 A1 | 3/2012 | Pianca et al. |
| 2012/0165911 A1 | 6/2012 | Pianca |
| 2012/0197375 A1 | 8/2012 | Pianca et al. |
| 2012/0203316 A1 | 8/2012 | Moffitt et al. |
| 2012/0203320 A1 | 8/2012 | Digiore et al. |
| 2012/0203321 A1 | 8/2012 | Moffitt et al. |
| 2012/0232354 A1 | 9/2012 | Ecker et al. |
| 2012/0253261 A1 | 10/2012 | Poletto et al. |
| 2012/0265262 A1 | 10/2012 | Osorio |
| 2012/0265268 A1 | 10/2012 | Blum et al. |
| 2012/0287420 A1 | 11/2012 | McLaughlin et al. |
| 2012/0314924 A1 | 12/2012 | Carlton et al. |
| 2012/0316615 A1 | 12/2012 | Digiore et al. |
| 2013/0019325 A1 | 1/2013 | Deisseroth et al. |
| 2013/0053905 A1 | 2/2013 | Wagner |
| 2013/0079848 A1 | 3/2013 | Campbell et al. |
| 2013/0102861 A1* | 4/2013 | Oki .................. A61N 5/062 600/314 |
| 2013/0105071 A1 | 5/2013 | Digiore et al. |
| 2013/0116744 A1 | 5/2013 | Blum et al. |
| 2013/0197424 A1 | 8/2013 | Bedenbaugh |
| 2013/0197602 A1 | 8/2013 | Pianca et al. |
| 2013/0261684 A1 | 10/2013 | Howard |
| 2013/0281819 A1 | 10/2013 | Schmid |
| 2013/0304152 A1 | 11/2013 | Bradley et al. |
| 2013/0317572 A1 | 11/2013 | Zhu et al. |
| 2013/0317573 A1 | 11/2013 | Zhu et al. |
| 2013/0317587 A1 | 11/2013 | Barker |
| 2013/0325091 A1 | 12/2013 | Pianca et al. |
| 2014/0039587 A1 | 2/2014 | Romero |
| 2014/0067015 A1 | 3/2014 | Kothandaraman et al. |
| 2014/0067023 A1 | 3/2014 | Register et al. |
| 2014/0114150 A1 | 4/2014 | Pogue et al. |
| 2014/0122379 A1 | 5/2014 | Moffitt et al. |
| 2014/0142664 A1 | 5/2014 | Roukes et al. |
| 2014/0163639 A1 | 6/2014 | Zhu |
| 2014/0200639 A1 | 7/2014 | De La Rama |
| 2014/0296953 A1 | 10/2014 | Pianca et al. |
| 2014/0343647 A1 | 11/2014 | Romero et al. |
| 2014/0353001 A1 | 12/2014 | Romero et al. |
| 2014/0358207 A1 | 12/2014 | Romero |
| 2014/0358208 A1 | 12/2014 | Howard et al. |
| 2014/0358209 A1 | 12/2014 | Romero et al. |
| 2014/0358210 A1 | 12/2014 | Howard et al. |
| 2015/0005860 A1 | 1/2015 | Howard et al. |
| 2015/0018915 A1 | 1/2015 | Leven |
| 2015/0021817 A1 | 1/2015 | Romero et al. |
| 2015/0045862 A1 | 2/2015 | Goldman et al. |
| 2015/0045864 A1 | 2/2015 | Howard |
| 2015/0051681 A1 | 2/2015 | Hershey |
| 2015/0066111 A1 | 3/2015 | Blum et al. |
| 2015/0066120 A1 | 3/2015 | Govea |
| 2015/0151113 A1 | 6/2015 | Govea et al. |
| 2015/0202456 A1 | 7/2015 | Andersen et al. |
| 2015/0290461 A1 | 10/2015 | Min et al. |
| 2015/0306414 A1 | 10/2015 | Nielsen et al. |
| 2015/0360031 A1 | 12/2015 | Bomzin et al. |
| 2015/0375006 A1 | 12/2015 | Denison et al. |
| 2016/0030749 A1 | 2/2016 | Carcier et al. |
| 2016/0045740 A1 | 2/2016 | Rezai et al. |
| 2016/0082251 A1 | 3/2016 | Moffitt et al. |
| 2016/0082253 A1 | 3/2016 | Moffitt et al. |
| 2016/0228692 A1 | 8/2016 | Steinke et al. |
| 2016/0256689 A1 | 9/2016 | Vallejo et al. |
| 2016/0271392 A1 | 9/2016 | Vallejo et al. |
| 2016/0271413 A1 | 9/2016 | Vallejo et al. |
| 2016/0287885 A1 | 10/2016 | Saini |
| 2016/0296745 A1 | 10/2016 | Govea et al. |
| 2016/0346557 A1 | 12/2016 | Bokil |
| 2016/0361543 A1 | 12/2016 | Kaula et al. |
| 2016/0375258 A1 | 12/2016 | Steinke |
| 2017/0061627 A1 | 3/2017 | Bokil |
| 2017/0095670 A1 | 4/2017 | Ghaffar et al. |
| 2017/0100580 A1 | 4/2017 | Olson |
| 2017/0136254 A1 | 5/2017 | Simon et al. |
| 2017/0225007 A1 | 8/2017 | Orinski |
| 2017/0259078 A1 | 9/2017 | Howard |
| 2017/0281966 A1 | 10/2017 | Basiony |
| 2017/0304633 A1 | 10/2017 | Zhang |
| 2017/0361108 A1 | 12/2017 | Leven |
| 2017/0361122 A1 | 12/2017 | Chabrol et al. |
| 2018/0028820 A1 | 2/2018 | Nageri |
| 2018/0064930 A1 | 3/2018 | Zhang et al. |
| 2018/0078776 A1 | 3/2018 | Mustakos et al. |
| 2018/0104482 A1 | 4/2018 | Bokil |
| 2018/0110971 A1 | 4/2018 | Serrano Carmona |
| 2018/0154152 A1 | 6/2018 | Chabrol et al. |
| 2018/0193655 A1 | 7/2018 | Zhang et al. |
| 2018/0229042 A1 | 8/2018 | Kaula et al. |
| 2018/0243570 A1 | 8/2018 | Malinowski et al. |
| 2018/0256906 A1 | 9/2018 | Pivonka et al. |
| 2018/0318578 A1 | 11/2018 | Ng et al. |
| 2018/0326219 A1 | 11/2018 | Wolf, II |
| 2018/0369606 A1 | 12/2018 | Zhang et al. |
| 2018/0369607 A1 | 12/2018 | Zhang et al. |
| 2018/0369608 A1 | 12/2018 | Chabrol |
| 2019/0209834 A1 | 7/2019 | Zhang et al. |
| 2019/0209849 A1 | 7/2019 | Hershey et al. |
| 2020/0094047 A1 | 3/2020 | Govea et al. |
| 2020/0155854 A1 | 5/2020 | Leven et al. |
| 2020/0271796 A1 | 8/2020 | Tahon et al. |
| 2020/0376262 A1 | 12/2020 | Clark et al. |
| 2021/0008388 A1 | 1/2021 | Vansickle et al. |
| 2021/0008389 A1 | 1/2021 | Featherstone et al. |
| 2021/0016111 A1 | 1/2021 | Vansickle et al. |

FOREIGN PATENT DOCUMENTS

| | | |
|---|---|---|
| WO | 2011150430 | 12/2011 |
| WO | 2012/103543 | 8/2012 |
| WO | 2014143387 | 9/2014 |
| WO | 2019/183054 | 9/2019 |
| WO | 2019/183068 | 9/2019 |
| WO | 2019/183075 | 9/2019 |
| WO | 2019/183078 | 9/2019 |

OTHER PUBLICATIONS

Chow, Roberta et al., Roberta et al., Inhibitory Effects of Laser Irradiation on Peripheral Mammalian Nerves and Relevance to Analgesic Effects: A Systematic Review, Photomedicine and Laser Surgery (2011) 29:6, 365-381.

Kono, Toru et al., Cord Dorsum Potentials Suppressed by Low Power Laser Irradiation on a Peripheral Nerve in the Cat, Journal of Clinical Laser Medicines Surgery (1993) 11:3, 115-118.

Snyder-Mackler, Lynn et al., Effect of Helium-Neon Laser Irradiation on Peripheral Sensory Nerve Latency, Phys. Ther. (1988), 68:223-225.

Darlot, Fannie et al., Near-infrared light is neuroprotective in a monkey model of Parkinson's disease (2006), 30 pages.

Micah S Siegel, Ehud Y Isacoff, A Genetically Encoded Optical Probe of Membrane Voltage, Neuron, vol. 19, Issue 4, Oct. 1997, pp. 735-741, ISSN 0896-6273, http://dx.doi.org/10.1016/30896-6273(00)80955-1.

Barnett L, Platisa J, Popovic M, Pieribone VA, Hughes T. A Fluorescent, Genetically-Encoded Voltage Probe Capable of Resolving Action Potentials. (2012) (http://www.sciencedirect.com/science/article/pii/S0896627300809551).

(56) References Cited

OTHER PUBLICATIONS

Brennan KC, Toga AW. Intraoperative Optical Imaging. In: Frostig RD, editor. In Vivo Optical Imaging of Brain Function. 2nd edition. Boca Raton (FL): CRC Press/Taylor & Francis; 2009. Chapter 13. Available from: http://www.ncbi.nlm.nih.gov/books/NBK20224/.
Use of NAD(P)H and flavoprotein autofluorescence transients to probe neuron and astrocyte responses to synaptic activation. Shuttleworth 2010 Neurochemestry international.
Vallejo, Ricardo, Kerry Bradley, and Leonardo Kapural. "Spinal cord stimulation in chronic pain: Mode of action." Spine 42 (2017): S53-S60.
Vivianne L. Tawfik, Su-Youne Chang, Frederick L. Hitti, David W. Roberts, James C. Leiter, Svetlana Jovanovic, Kendall H. Lee, Deep Brain Stimulation Results in Local Glutamate and Adenosine Release: Investigation Into the Role of Astrocytes, Neurosurgery, vol. 67, Issue 2, Aug. 2010, pp. 367-375, https://doi.org/10.1227/01.NEU.0000371988.73620.4C.
International Search Report and Written Opinion for PCT Application No. PCT/US2019/022917 dated May 21, 2019.

\* cited by examiner

OPTICAL STIMULATION SYSTEMS WITH CALIBRATION AND METHODS OF MAKING AND USING

CROSS-REFERENCE TO RELATED APPLICATIONS

This application is the U.S. national stage application of PCT Application No. PCT/US19/22917, filed Mar. 19, 2019, which claims the benefit under 35 U.S.C. § 119(e) of U.S. Provisional Patent Application Ser. No. 62/647,561, filed Mar. 23, 2018, both of which are incorporated herein by reference.

FIELD

The present disclosure is directed to the area of implantable optical stimulation systems and methods of making and using the systems. The present disclosure is also directed to implantable optical stimulation systems utilizing a calibration table or calibration formula as well as methods of making and using the optical stimulation systems.

BACKGROUND

Implantable optical stimulation systems can provide therapeutic benefits in a variety of diseases and disorders. For example, optical stimulation can be applied to the brain either externally or using an implanted stimulation lead to provide, for example, deep brain stimulation, to treat a variety of diseases or disorders. Optical stimulation may also be combined with electrical stimulation.

Stimulators have been developed to provide therapy for a variety of treatments. A stimulator can include a control module (for generating light or electrical signals sent to light sources in a lead), one or more leads, and one or more light sources coupled to, or disposed within, each lead. The lead is positioned near the nerves, muscles, brain tissue, or other tissue to be stimulated.

BRIEF SUMMARY

In one aspect, an optical stimulation system includes a light source; an optical lead coupled, or coupleable, to the light source; at least one of a calibration table or a calibration formula, wherein the at least one of the calibration table or the calibration formula is generated by a calibration procedure specifically using the light source and the optical lead of the optical stimulation system; and a control unit coupled, or coupleable, to the light source. The control module includes a memory to store the at least one of the calibration table or the calibration formula, and a processor coupled to the memory and configured for receiving a target light output level, using the at least one of the calibration table or the calibration formula to determine at least one operational parameter for generating the target light output level, and directing the light source, using the at least one operational parameter, to generate light at the target light output level. In at least some aspects, the light source is part of the optical lead.

In at least some aspects, the optical stimulation system further includes a light monitor coupled, or coupleable to, the control unit, wherein the optical lead further includes a first optical waveguide to receive light generated by the light source and emit the light from a distal portion of the optical lead and a second optical waveguide configured to receive a portion of the light emitted from the distal portion of the optical lead and direct the received portion of the light to the light monitor. In at least some aspects, the processor is further configured for receiving a measurement from the light monitor in response to generation of light at the optical output level; and comparing the measurement to the target light output value. In at least some aspects, the processor is further configured for modifying the at least one operational parameter based on the comparison between the measurement and the target light output value.

In at least some aspects, the at least one of the calibration table or the calibration formula includes a relationship between measurement values of the light monitor and light output values at the distal portion of the optical lead. In at least some aspects, the at least one of the calibration table or the calibration formula includes a relationship between measurement values of the light monitor and values of the at least one operational parameter. In at least some aspects, the at least one operational parameter is an amplitude of signal provided to the light source to generate the light. In at least some aspects, the processor is further configured for receiving a request for measurement of light output; directing the light monitor to measure the light output; using the at least one of the calibration table or the calibration formula to determine a light output level; and reporting the light output value.

In at least some aspects, the at least one of the calibration table or the calibration formula includes a relationship between light output values at the distal portion of the optical lead and values of the at least one operational parameter. In at least some aspects, the at least one operational parameter is an amplitude of signal provided to the light source to generate the light.

In another aspect, a non-transitory processor readable storage media includes instructions for optical stimulation using an optical stimulation system including a light source and an optical lead, wherein execution of the instructions by one or more processor devices performs actions including receiving a target light output level; using the at least one of a calibration table or a calibration formula to determine at least one operational parameter for generating the target light output level, wherein the at least one of the calibration table or the calibration formula is generated by a calibration procedure specifically using the light source and the optical lead of the optical stimulation system; and directing the light source, using the at least one operational parameter, to generate light at the target light output level.

In a further aspect, a method for optical stimulation using an optical stimulation system including a light source and an optical lead includes receiving a target light output level; using the at least one of a calibration table or a calibration formula to determine at least one operational parameter for generating the target light output level, wherein the at least one of the calibration table or the calibration formula is generated by a calibration procedure specifically using the light source and the optical lead of the optical stimulation system; and directing the light source, using the at least one operational parameter, to generate light at the target light output level.

In at least some aspects of the non-transitory processor readable storage media or the method, the actions or steps further include receiving a measurement from a light monitor in response to generation of light at the optical output level; and comparing the measurement to the target light output value. In at least some aspects of the non-transitory processor readable storage media or the method, the actions or steps further include modifying the at least one operational parameter based on the comparison between the measurement and the target light output value.

In at least some aspects of the non-transitory processor readable storage media or the method, the at least one of the calibration table or the calibration formula includes a relationship between measurement values of the light monitor and light output values at the distal portion of the optical lead. In at least some aspects of the non-transitory processor readable storage media or the method, the at least one of the calibration table or the calibration formula includes a relationship between measurement values of the light monitor and values of the at least one operational parameter. In at least some aspects of the non-transitory processor readable storage media or the method, the at least one operational parameter is an amplitude of signal provided to the light source to generate the light.

In yet another aspect, a method of calibrating an optical stimulation system including a light source and an optical lead includes generating light using the light source and different values of an operational parameter; measuring a light output value for each of the different values of the operational parameter; and generating at least one of a calibration table or a calibration formula for the optical stimulation system using the measured light output values and the different values of the operational parameter.

In at least some aspects, the operational parameter is an amplitude of signal provided to the light source to generate the light. In at least some aspects, the at least one of the calibration table or the calibration formula includes a relationship between measurement values of the light monitor and light output values at the distal portion of the optical lead. In at least some aspects, the at least one of the calibration table or the calibration formula includes a relationship between measurement values of the light monitor and values of the at least one operational parameter.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to the area of implantable optical stimulation systems and methods of making and using the systems. The present disclosure is also directed to implantable optical stimulation systems utilizing a calibration table or calibration formula as well as methods of making and using the optical stimulation systems.

In some embodiments, the implantable optical stimulation system only provides optical stimulation. In other embodiments, the stimulation system can include both optical and electrical stimulation. In at least some of these embodiments, the optical stimulation system can be a modification of an electrical stimulation system to also, or instead, provide optical stimulation. Optical stimulation may include, but is not necessarily limited to, stimulation resulting from response to particular wavelengths or wavelength ranges of light or from thermal effects generated using light or any combination thereof.

Figure 1:
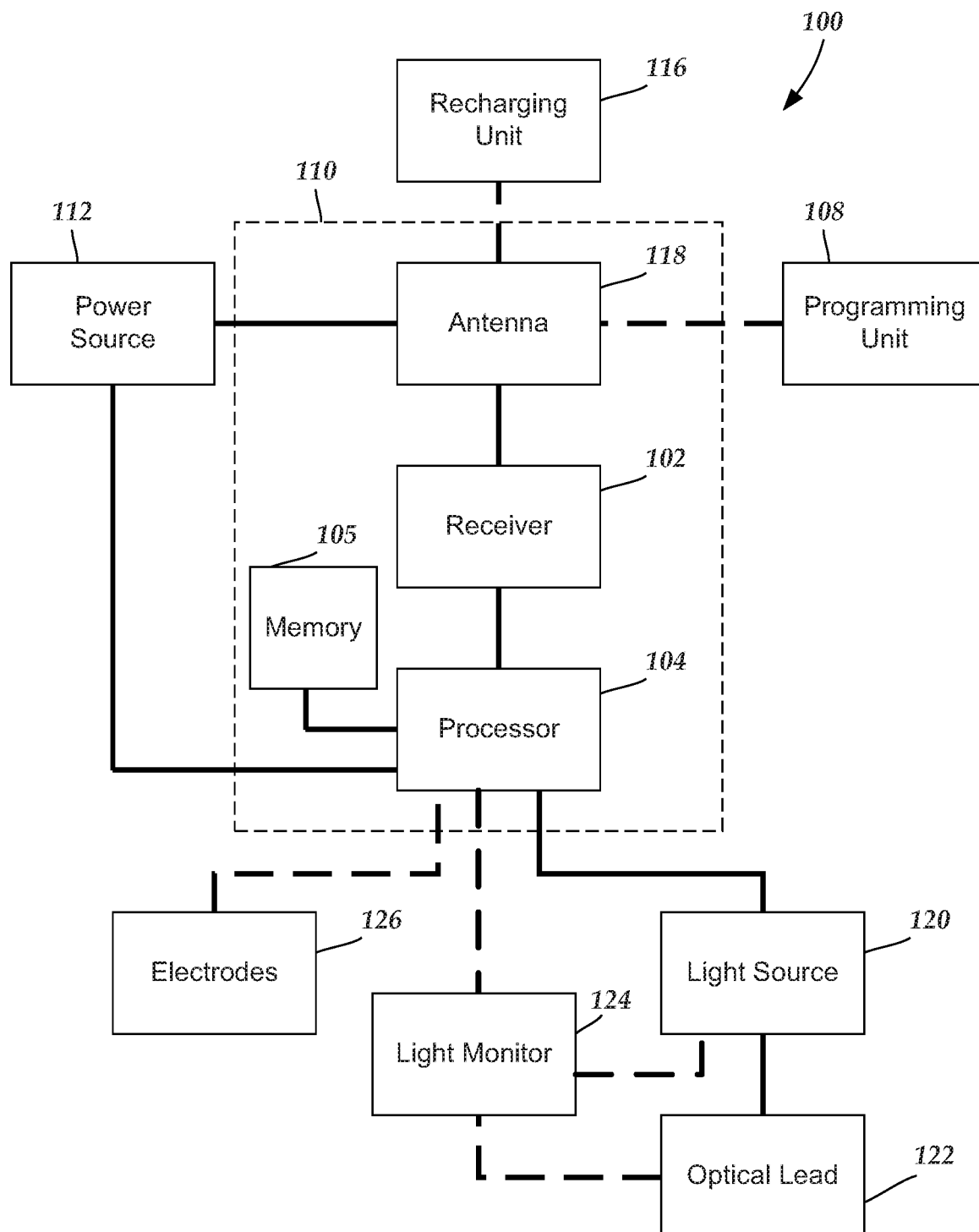
FIG. 1 is a schematic overview of one embodiment of components of an optical or optical/electrical stimulation system, including an electronic subassembly.

FIG. 1 is a schematic overview of one embodiment of components of an optical stimulation system 100 (or combination optical/electrical stimulation system) including an electronic subassembly 110 disposed within a control module (for example, an implantable or external pulse generator or implantable or external light generator). It will be understood that the optical stimulation system can include more, fewer, or different components and can have a variety of different configurations including those configurations disclosed in the stimulator references cited herein. In at least some embodiments, the optical stimulation system may also be capable of providing electrical stimulation through optional electrodes 126.

In at least some embodiments, selected components (for example, a power source 112, an antenna 118, a receiver 102, a processor 104, and a memory 105) of the optical stimulation system can be positioned on one or more circuit boards or similar carriers within a sealed housing of a control module. Any suitable processor 104 can be used and can be as simple as an electronic device that, for example, produces signals to direct or generate optical stimulation at a regular interval or the processor can be capable of receiving and interpreting instructions from an external programming unit 108 that, for example, allows modification of stimulation parameters or characteristics.

The processor 104 is generally included to control the timing and other characteristics of the optical stimulation system. For example, the processor 104 can, if desired, control one or more of the timing, pulse frequency, amplitude, and duration of the optical stimulation. In addition, the processor 104 can select one or more of the optional electrodes 126 to provide electrical stimulation, if desired. In some embodiments, the processor 104 selects which of the optional electrode(s) are cathodes and which electrode(s) are anodes.

Any suitable memory 105 can be used. The memory 105 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, magnetic storage devices, or any other medium which can be used to store the desired information and which can be accessed by a processor.

The processor 104 is coupled to a light source 120. Any suitable light source can be used including, but not limited to, light emitting diodes (LEDs), organic light emitting diodes (OLEDs), laser diodes, lamps, light bulbs, or the like or any combination thereof. In at least some embodiments, the optical stimulation system may include multiple light sources. In at least some embodiments, each of the multiple light sources may emit light having a different wavelength or different wavelength range. Any suitable wavelength or wavelength range can be used including, but not limited to, visible, near infrared, and ultraviolet wavelengths or wavelength ranges. In at least some embodiments, the optical stimulation system includes a light source that emits in the orange, red, or infrared wavelength ranges (for example, in the range of 600 to 1200 nm or in the range of 600 to 700 nm or in the range of 610 to 650 nm or 620 nm or the like.) In at least some embodiments, the optical stimulation system includes a light source that emits in the green or blue wavelength ranges (for example, in the range of 450 to 550 nm or in the range of 495 to 545 nm or the like.) A wavelength or wavelength range of a light source may be selected to obtain a specific therapeutic, chemical, or biological effect.

As described below, the light source 120 may be disposed within the control module or disposed external to the control module such as, for example, in a separate unit or module or as part of an optical lead. The processor 104 provides electrical signals to operate the light source 120 including, for example, directing or driving the generation of light by the light source, pulsing the light source, or the like. For example, the processor 104 can direct current from the power source 112 to operate the light source 120. In at least some embodiments, the light source 120 is coupled to one or more optical waveguides (such as an optical fiber or other optical transmission media) disposed in an optical lead 122. In at least some embodiments, the optical lead 122 is arranged so that one or more of the optical waveguides emits light from the distal portion of the optical lead (for example, the distal end or at one or more positions along the distal portion of the lead or any combination thereof).

Optionally, the processor 104 is also coupled to a light monitor 124 that is used to monitor or measure light from the light source 122. For example, the light monitor 124 can produce electrical or other signals in response to the light received by the light monitor. Any suitable light monitor 124 can be used including, but not limited to, photodiodes, phototransistors, photomultipliers, charge coupled devices (CCDs), light dependent resistors (LRDs), photo-emissive cells, photo-conductive ells, photo-voltaic cells, photo-junction devices, or the like or any combination thereof. The light monitor 124 may be used to measure or monitor the light emitted by the light source 120 or from the optical waveguide(s) (or other optical transmission media) of the optical lead 122. In at least some embodiments, the light monitor 124 may be coupled to one or more optical waveguides (or other optical transmission media) of the optical lead 122 to transmit the light along an optical lead for measurement or monitoring.

Any power source 112 can be used including, for example, a battery such as a primary battery or a rechargeable battery. Examples of other power sources include super capacitors, nuclear or atomic batteries, fuel cells, mechanical resonators, infrared collectors, flexural powered energy sources, thermally-powered energy sources, bioenergy power sources, bioelectric cells, osmotic pressure pumps, and the like. As another alternative, power can be supplied by an external power source through inductive coupling via an antenna 118 or a secondary antenna. The external power source can be in a device that is mounted on the skin of the user or in a unit that is provided near the user on a permanent or periodic basis. In at least some embodiments, if the power source 112 is a rechargeable battery, the battery may be recharged using the antenna 118 and a recharging unit 116. In some embodiments, power can be provided to the battery for recharging by inductively coupling the battery to the external recharging unit 116.

In at least some embodiments, the processor 104 is coupled to a receiver 102 which, in turn, is coupled to an antenna 118. This allows the processor 104 to receive instructions from an external source, such as programming unit 108, to, for example, direct the stimulation parameters and characteristics. The signals sent to the processor 104 via the antenna 118 and the receiver 102 can be used to modify or otherwise direct the operation of the optical stimulation system. For example, the signals may be used to modify the stimulation characteristics of the optical stimulation system such as modifying one or more of stimulation duration and stimulation amplitude. The signals may also direct the optical stimulation system 100 to cease operation, to start operation, to start charging the battery, or to stop charging the battery. In other embodiments, the stimulation system does not include the antenna 118 or receiver 102 and the processor 104 operates as initially programmed.

In at least some embodiments, the antenna 118 is capable of receiving signals (e.g., RF signals) from an external programming unit 108 (such as a clinician programmer or patient remote control or any other device) which can be programmed by a user, a clinician, or other individual. The programming unit 108 can be any unit that can provide information or instructions to the optical stimulation system 100. In at least some embodiments, the programming unit 108 can provide signals or information to the processor 104 via a wireless or wired connection. One example of a suitable programming unit is a clinician programmer or other computer operated by a clinician or other user to select, set, or program operational parameters for the stimulation. Another example of the programming unit 108 is a remote control such as, for example, a device that is worn on the skin of the user or can be carried by the user and can have a form similar to a pager, cellular phone, or remote control, if desired. In at least some embodiments, a remote control used by a patient may have fewer options or capabilities for altering stimulation parameters than a clinician programmer.

Optionally, the optical stimulation system 100 may include a transmitter (not shown) coupled to the processor 104 and the antenna 118 for transmitting signals back to the programming unit 108 or another unit capable of receiving the signals. For example, the optical stimulation system 100 may transmit signals indicating whether the optical stimulation system 100 is operating properly or not or indicating when the battery needs to be charged or the level of charge remaining in the battery. The processor 104 may also be capable of transmitting information about the stimulation characteristics so that a user or clinician can determine or verify the characteristics.

Figure 2:
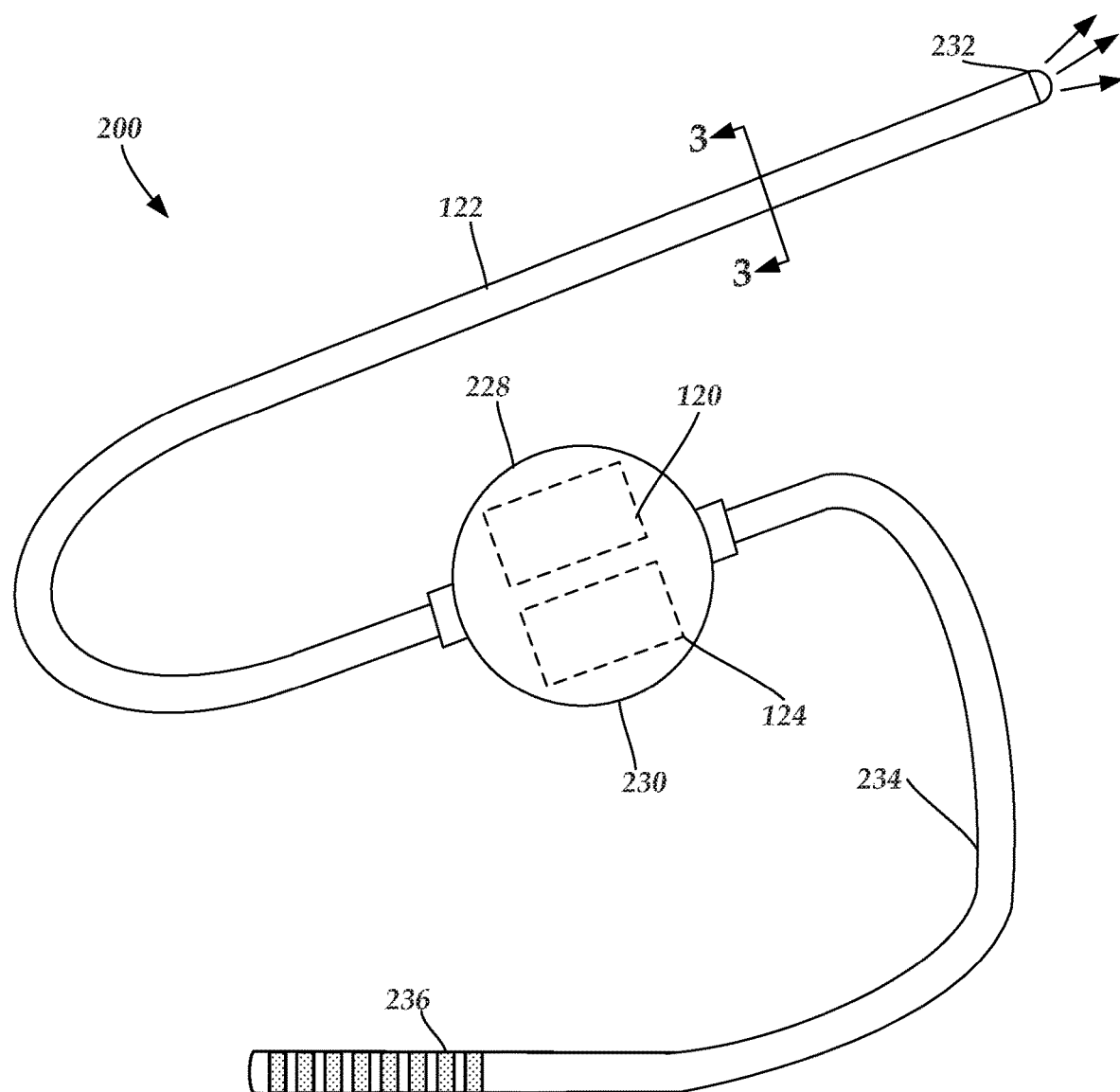
FIG. 2 is a schematic side view of one embodiment of an arrangement including a light source, an optional light monitor, an optical lead, and a connector lead.
Figure 3:
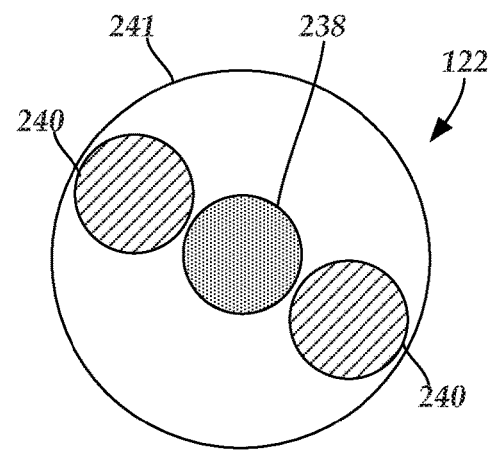
FIG. 3 is a schematic cross-sectional view of one embodiment of the optical lead of FIG. 2.

FIG. 2 illustrates one embodiment of an arrangement 200 for an optical stimulation system that can be used with a control module (see, FIG. 4). In at least some embodiments, the control module may be originally designed for use with an electrical stimulation system and adapted for use as an optical stimulation system via the arrangement 200.

The arrangement 200 includes a base unit 228 a light source 120 disposed in a housing 230, an optical lead 122 with one or more emission regions 232a, 232b of a distal portion from which light is emitted, and a connector lead 234 with one or more terminals 236 for coupling to a control module or lead extension, as described below. The optical lead 122 and connector lead 234, independently, may be permanently, or removably, coupled to the base unit 228. If removably coupleable to the base unit 228, the optical lead 122, connector lead 234, or both will have corresponding arrangements (for example, terminals and contacts) for transmission of light (for the optical lead) or electrical signals (for the connector lead) to the base unit 228. The one or more emission regions 232a, 232b may include a tip emission region 232a that emits distally away from the lead or may include a side emission regions 232b that emit at the sides of the lead or any combination thereof.

In addition to the light source 120, the base unit 228 can optionally include a light monitor 124. The base unit 228 may also include components such as electrical components associated with the light source 120 or light monitor 124, a heat sink, optical components (for example, a lens, polarizer, filter, or the like), a light shield to reduce or prevent light emission out of the housing of the base unit or to reduce or prevent extraneous light from penetrating to the light monitor 124 or the like. The housing 230 of the base unit 228 can be made of any suitable material including, but not limited to, plastic, metal, ceramic, or the like, or any combination thereof. If the base unit 228 is to be implanted, the housing 230 is preferably made of a biocompatible material such as, for example, silicone, polyurethane, titanium or titanium alloy, or any combination thereof.

In at least some embodiments, the optical lead 122, as illustrated in cross-section in Figured 3, includes a lead body 241 and one or more optical waveguides 238 (or other optical transmission media) for transmission of light from the light source 120 with emission along the one or more emission regions 232a, 232b disposed on the distal portion of the optical lead. In the illustrated embodiment, the light is emitted at the distal tip of the lead. In other embodiments, the light may be emitted at one or more points along the length of at least the distal portion of the lead. In some embodiments with multiple light sources, there may be separate optical waveguides for each light source or light from multiple light sources may be transmitted along the same optical waveguide(s). The optical lead 122 may also include one or more optical components, such as a lens, diffuser, polarizer, filter, or the like, at the distal portion of the lead (for example, at the terminal end of the optical waveguide 238) to modify the light transmitted through the optical waveguide.

In at least some embodiments that include a light monitor 124, the optical lead 122 may include one or more optical waveguides 240 (or other optical transmission media) that receive light emitted from the light source 120 and transmitted by the optical waveguide 238 in order to measure or monitor the light emitted at the one or more emission regions 232a, 232b of the optical lead. The optical waveguide(s) 240 transmit light from the one or more emission regions 232a, 232b of the optical lead to the light monitor 124 in the base unit 228. The optical lead 122 may also include one or more optical components, such as a lens, diffuser, polarizer, filter, or the like, at the distal portion of the lead (for example, at the terminal end of the optical waveguide 240) to modify the light received by the optical waveguide(s) 240.

The connector lead 234 includes conductors (e.g., wires—not shown) disposed in a lead body extending along the connector lead 234 to the terminals 236 on the proximal end of the connector lead. As an alternative, the connector lead 234 may be permanently attached to a control module or other device where the conductors then attach to contact points within the control module or other device. The conductors carry electrical signals to the base unit 228 and the light source 120 and, optionally, other electrical components in the base unit for operation of the light source 120. The conductors may also carry electrical signals from the optional light monitor 124 in the base unit 228 to the control module or other device. These electrical signals may be generated by the light monitor 124 in response to light received by the light monitor.

Figure 4A:
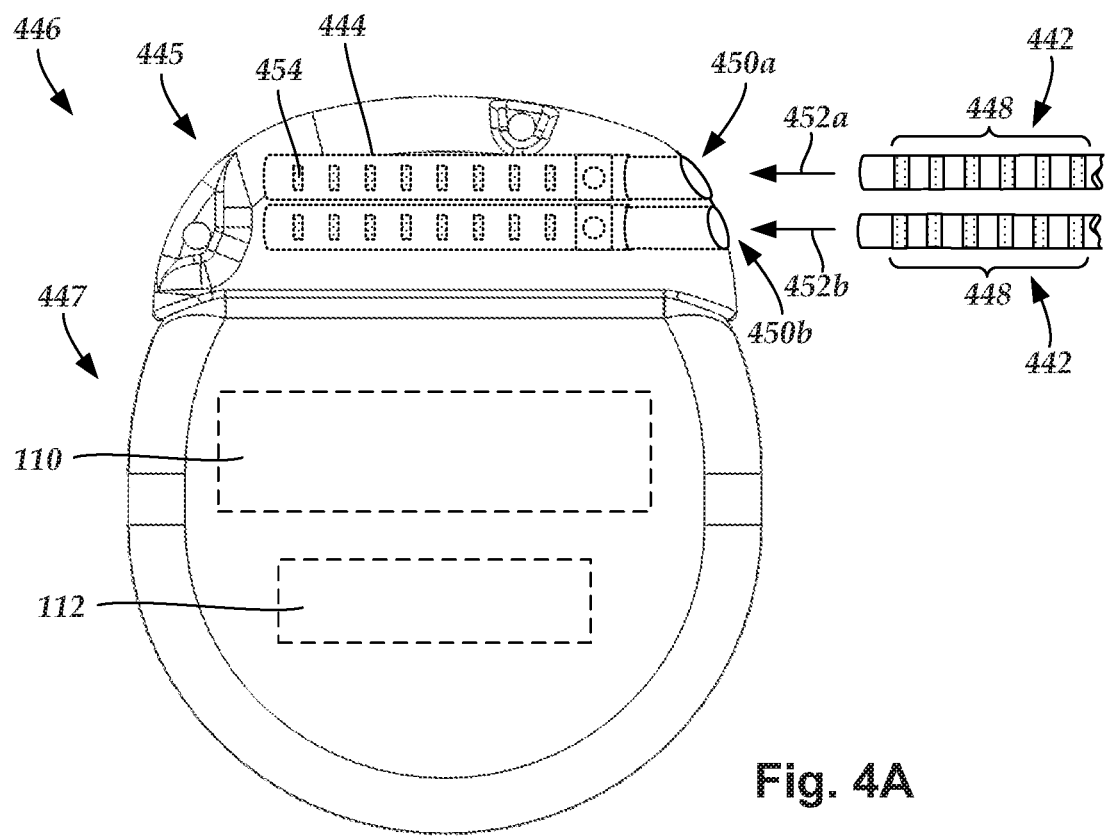
FIG. 4A is a schematic side view of one embodiment of a control module configured to electrically couple to a lead or lead extension.

FIG. 4A is a schematic side view of one embodiment of proximal ends 442 of one or more leads (for example, connector lead 234 of FIG. 2) or lead extensions 460 (see, FIG. 4B) coupling to a control module 446 (or other device) through one or more control module connectors 444. The one or more proximal ends 442 include terminals 448 (for example, terminals 236 of connector lead 234).

The control module connector 444 defines at least one port 450a, 450b into which a proximal end 442 can be inserted, as shown by directional arrows 452a and 452b. The control module 446 (or other device) can define any suitable number of ports including, for example, one, two, three, four, five, six, seven, eight, or more ports.

The control module connector 444 also includes a plurality of connector contacts, such as connector contact 454, disposed within each port 450a and 450b. When the proximal end 442 is inserted into the ports 450a and 450b, the connector contacts 454 can be aligned with a plurality of terminals 448 disposed along the proximal end(s) 442. Examples of connectors in control modules are found in, for example, U.S. Pat. Nos. 7,244,150 and 8,224,450, which are incorporated by reference.

The control module 446 typically includes a connector housing 445 and a sealed electronics housing 447. An electronic subassembly 110 (see, FIG. 1) and an optional power source 112 (see, FIG. 1) are disposed in the electronics housing 447.

Figure 4B:
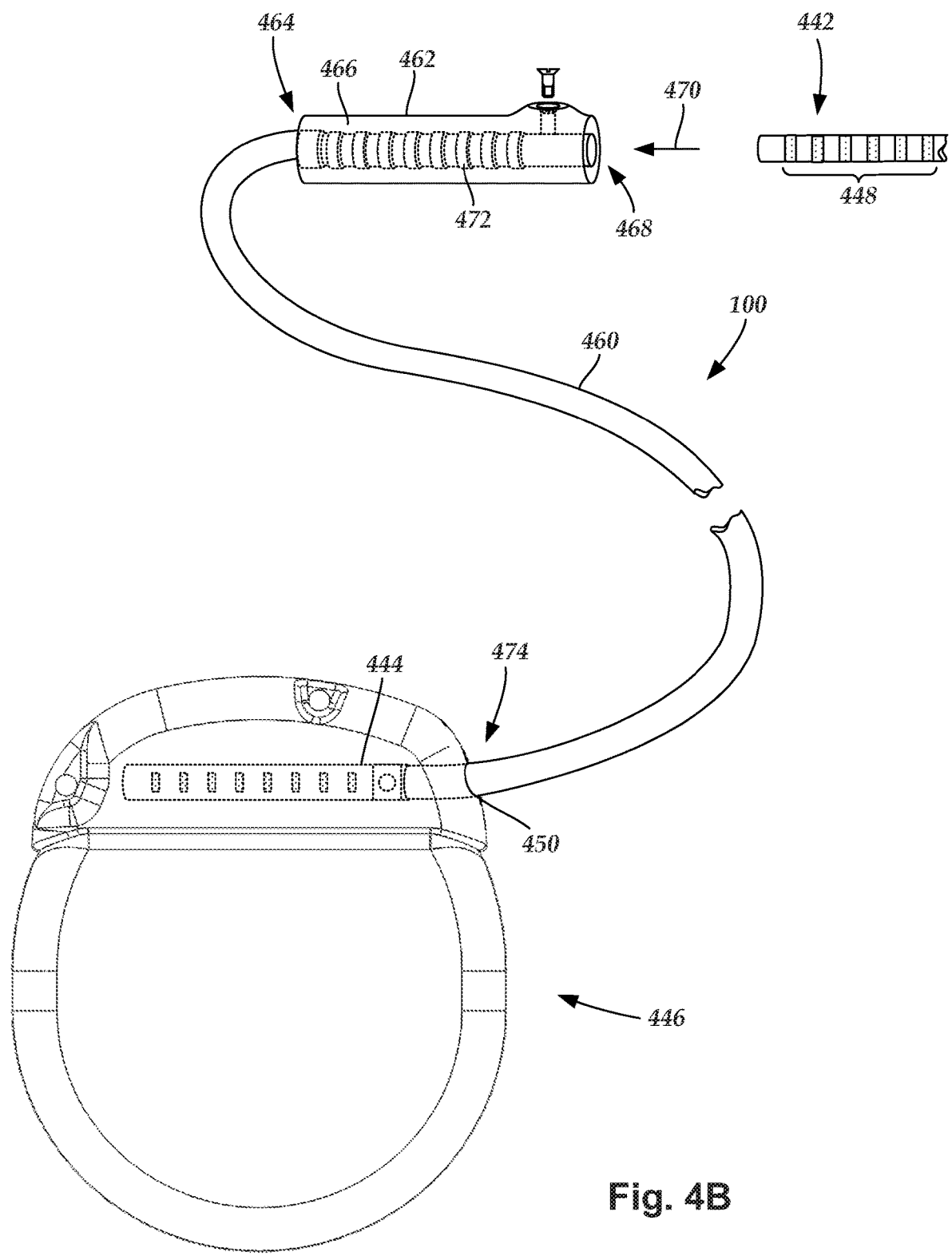
FIG. 4B is a schematic side view of one embodiment of a lead extension configured to electrically couple a lead to the control module of FIG. 4A.

FIG. 4B is a schematic side view of a portion of another embodiment of an optical stimulation system 100. The optical stimulation system 100 includes a lead extension 460 that is configured to couple one or more proximal ends 442 of a lead to the control module 446. In FIG. 4B, the lead extension 460 is shown coupled to a single port 450 defined in the control module connector 444. Additionally, the lead extension 460 is shown configured to couple to a single proximal end 442 of a lead (for example, the connector lead 234 of FIG. 2).

A lead extension connector 462 is disposed on the lead extension 460. In FIG. 4B, the lead extension connector 462 is shown disposed at a distal end 464 of the lead extension 460. The lead extension connector 462 includes a connector housing 466. The connector housing 466 defines at least one port 468 into which terminals 448 of the proximal end 442 of the lead can be inserted, as shown by directional arrow 470. The connector housing 466 also includes a plurality of connector contacts, such as connector contact 472. When the proximal end 442 is inserted into the port 468, the connector contacts 472 disposed in the connector housing 466 can be aligned with the terminals 448 for electrical coupling.

In at least some embodiments, the proximal end 474 of the lead extension 460 is similarly configured as a proximal end 442 of a lead. The lead extension 460 may include a plurality of electrically conductive wires (not shown) that electrically couple the connector contacts 472 to a proximal end 474 of the lead extension 460 that is opposite to the distal end 464. In at least some embodiments, the conductive wires disposed in the lead extension 460 can be electrically coupled to a plurality of terminals (not shown) disposed along the proximal end 474 of the lead extension 460. In at least some embodiments, the proximal end 474 of the lead extension 460 is configured for insertion into a connector disposed in another lead extension (or another intermediate device). In other embodiments (and as shown in FIG. 4B), the proximal end 474 of the lead extension 460 is configured for insertion into the control module connector 144.

Figure 5:
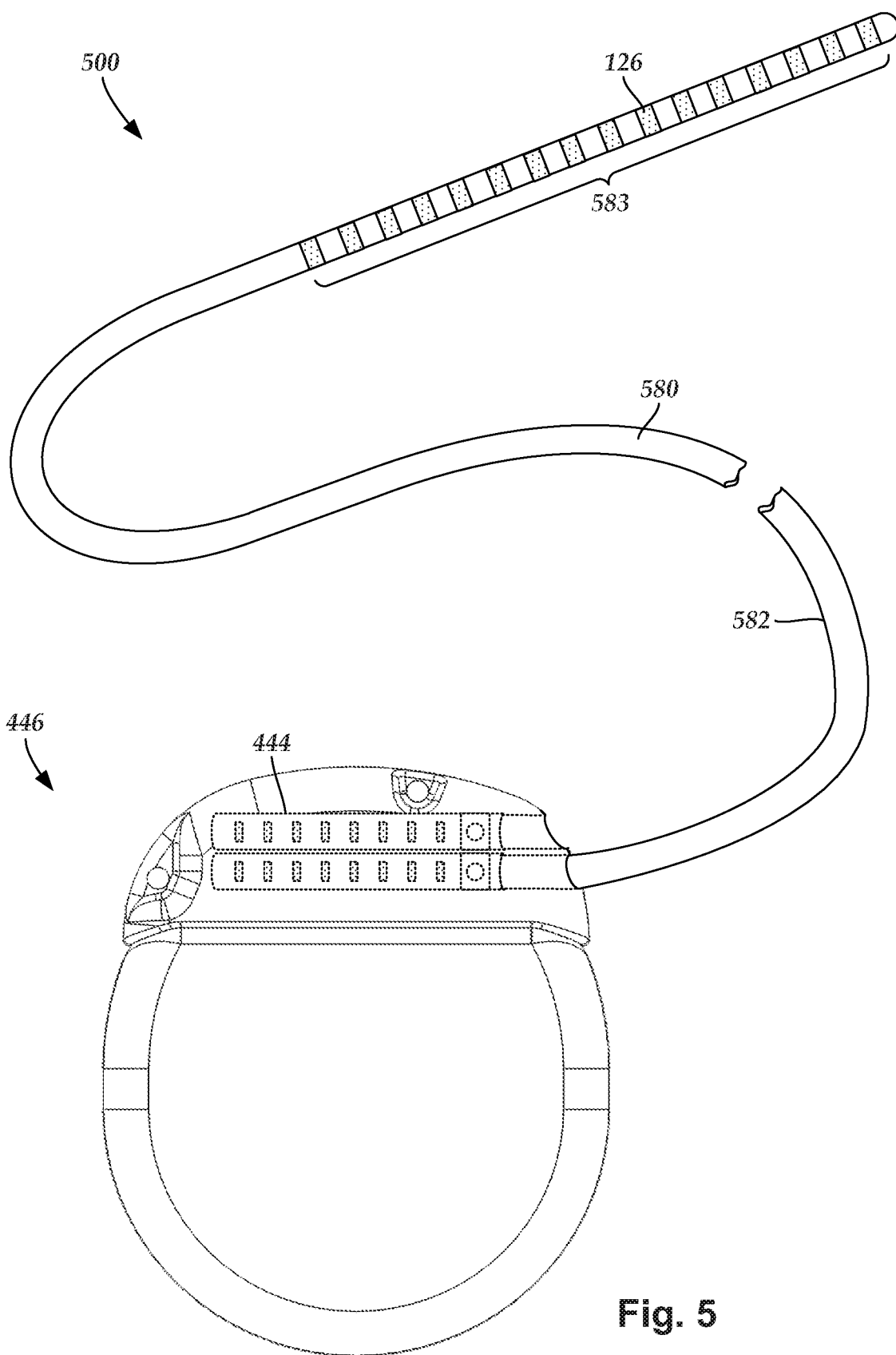
FIG. 5 is a schematic side view of one embodiment of an electrical stimulation system that includes an electrical stimulation lead electrically coupled to a control module.

In some embodiments, the optical stimulation system may also be an electrical stimulation system. FIG. 5 illustrates schematically one embodiment of an electrical stimulation system 500. The electrical stimulation system includes a control module 446 (e.g., a stimulator or pulse generator) and an electrical stimulation lead 580 coupleable to the control module 446. The same control module 446 can be utilized with the arrangement 200 (FIG. 2) for optical stimulation and an electrical stimulation lead 580. With respect to the optical/electrical stimulation system of FIG. 1, the control module 446 can include the electronic subassembly 110 (FIG. 1) and power source 112 (FIG. 1) and the electrical stimulation lead 580 can include the electrodes 126. The optical arrangement 200 of FIG. 2 can be inserted into another port of the control module 446.

The lead 580 includes one or more lead bodies 582, an array of electrodes 583, such as electrode 126, and an array of terminals (e.g., 448 in FIG. 4A-4B) disposed along the one or more lead bodies 582. In at least some embodiments, the lead is isodiametric along a longitudinal length of the lead body 582. Electrically conductive wires, cables, or the like (not shown) extend from the terminals to the electrodes 126. Typically, one or more electrodes 126 are electrically coupled to each terminal. In at least some embodiments, each terminal is only connected to one electrode 126.

The lead 580 can be coupled to the control module 446 in any suitable manner. In at least some embodiments, the lead 580 couples directly to the control module 446. In at least some other embodiments, the lead 580 couples to the control module 446 via one or more intermediate devices. For example, in at least some embodiments one or more lead extensions 460 (see e.g., FIG. 4B) can be disposed between the lead 580 and the control module 446 to extend the distance between the lead 580 and the control module 446. Other intermediate devices may be used in addition to, or in lieu of, one or more lead extensions including, for example, a splitter, an adaptor, or the like or combinations thereof. It will be understood that, in the case where the electrical stimulation system 500 includes multiple elongated devices disposed between the lead 580 and the control module 446, the intermediate devices may be configured into any suitable arrangement.

The electrical stimulation system or components of the electrical stimulation system, including one or more of the lead bodies 582 and the control module 446, are typically implanted into the body of a patient. The electrical stimulation system can be used for a variety of applications including, but not limited to, brain stimulation, neural stimulation, spinal cord stimulation, muscle stimulation, and the like.

The electrodes 126 can be formed using any conductive, biocompatible material. Examples of suitable materials include metals, alloys, conductive polymers, conductive carbon, and the like, as well as combinations thereof. In at least some embodiments, one or more of the electrodes 126 are formed from one or more of: platinum, platinum iridium, palladium, palladium rhodium, or titanium. The number of electrodes 126 in each array 583 may vary. For example, there can be two, four, six, eight, ten, twelve, fourteen, sixteen, or more electrodes 126. As will be recognized, other numbers of electrodes 126 may also be used.

Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties.

Figure 6:
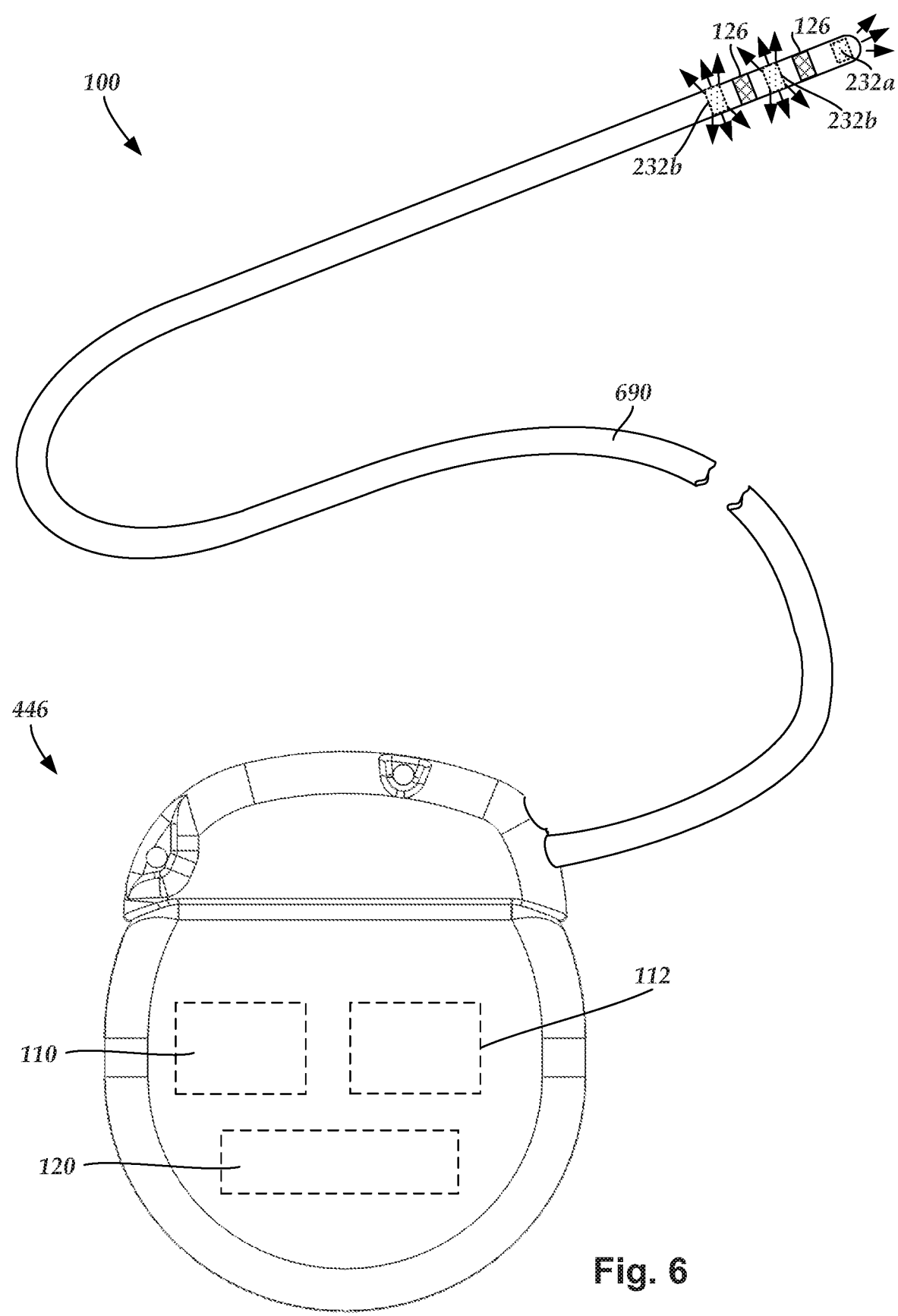
FIG. 6 is a schematic side view of one embodiment of an optical/electrical stimulation system with an optical/electrical stimulation lead coupled to a control module having a light source.

FIG. 6 illustrates other optional embodiments. For example, FIG. 6 illustrates one embodiment of an optical/electrical stimulation system 100 with a lead 690 with both electrodes 126 and an optical waveguide that emits light from the from one more emission regions 232a, 232b of the lead. In some embodiments, the lead 690 can be coupled to the base unit 228 and connector lead 234 of FIG. 2 with conductors (and optionally connector contacts if the lead 690 or connector lead 234 are removable from the base unit 228) electrically coupling the terminals 236 of the connector lead to the electrodes 126 of the lead 690.

FIG. 6 also illustrates one embodiment of a control module 446 that also includes a light source 120 within the control module. Such an arrangement can replace the base unit 228 and connector lead 234 of FIG. 2 and may include a lead extension 460.

Figure 7:
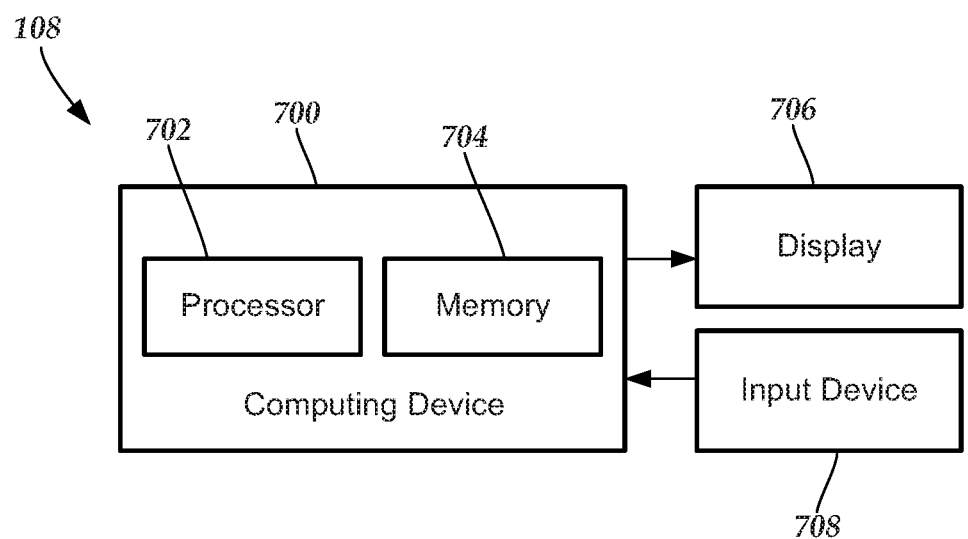
FIG. 7 is a schematic overview of one embodiment of components of a programming unit for an optical or optical/electrical stimulation system.

FIG. 7 illustrates one embodiment of a programming unit 108. The programming unit 108 can include a computing device 700 or any other similar device that includes a processor 702 and a memory 704, a display 706, and an input device 708.

The computing device 700 can be a computer, tablet, mobile device, or any other suitable device for processing information or programming an optical stimulation system. The computing device 700 can be local to the user or can include components that are non-local to the computer including one or both of the processor 702 or memory 704 (or portions thereof). For example, in at least some embodiments, the user may operate a terminal that is connected to a non-local computing device. In other embodiments, the memory can be non-local to the user.

The computing device 700 can utilize any suitable processor 702 including at least one hardware processors that may be local to the user or non-local to the user or other components of the computing device. The processor 702 is configured to execute instructions provided to the processor 702, as described below.

Any suitable memory 704 can be used for the computing device 702. The memory 704 illustrates a type of computer-readable media, namely computer-readable storage media. Computer-readable storage media may include, but is not limited to, nonvolatile, non-transitory, removable, and non-removable media implemented in any method or technology for storage of information, such as computer readable instructions, data structures, program modules, or other data. Examples of computer-readable storage media include RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

Communication methods provide another type of computer readable media; namely communication media. Communication media typically embodies computer-readable instructions, data structures, program modules, or other data in a modulated data signal such as a carrier wave, data signal, or other transport mechanism and include any information delivery media. The terms "modulated data signal," and "carrier-wave signal" includes a signal that has at least one of its characteristics set or changed in such a manner as to encode information, instructions, data, and the like, in the signal. By way of example, communication media includes wired media such as twisted pair, coaxial cable, fiber optics, wave guides, and other wired media and wireless media such as acoustic, RF, infrared, and other wireless media.

The display 706 can be any suitable display device, such as a monitor, screen, display, or the like, and can include a printer. In at least some embodiments, the display 706 may form a single unit with the computing device 700. The input device 708 can be, for example, a keyboard, mouse, touch screen, track ball, joystick, voice recognition system, or any combination thereof, or the like.

The methods and systems described herein may be embodied in many different forms and should not be construed as limited to the embodiments set forth herein. Accordingly, the methods and systems described herein may take the form of an entirely hardware embodiment, an entirely software embodiment or an embodiment combining software and hardware aspects. Systems referenced herein typically include memory and typically include methods for communication with other devices including mobile devices. Methods of communication can include both wired and wireless (for example, RF, optical, or infrared) communications methods and such methods provide another type of computer readable media; namely communication media. Wired communication can include communication over a twisted pair, coaxial cable, fiber optics, wave guides, or the like, or any combination thereof. Wireless communication can include RF, infrared, acoustic, near field communication, Bluetooth™, or the like, or any combination thereof.

This optical power output by the light source 120 is often different from the optical power output at the distal end of the optical lead. For example, the components in the light source 120 and optical lead 122, as well as the manufacturing process, produce light losses from the optical power output at the distal end of the optical lead. Moreover, the individual light sources and optional light monitors, as well as other optical components such as the optical waveguides, generally have variations of performance from part to part. In addition, the power source 112 can have an associated tolerance and can vary between individual units.

To provide more uniform controlled output for therapy, an optical stimulation system can include a mechanism to provide calibration for the system. In at least some embodiments, a user may be allowed to program custom calibrations of the optical stimulation system (or components of the optical stimulation system) dynamically when the system is implanted into the patient, or before. In at least some embodiments, calibration of optical energy output can be performed during, or subsequent to, manufacturing. In at least some embodiments where the power source and the light source (or other optical components) are independently manufactured, multiple components can be individually calibrated and may be packaged together with a combined calibration.

In at least some embodiments, one or more calibration tables or calibration formulas can be stored in the memory 105 of the optical stimulation system 100 (for example, a memory within the control module 446 or the memory 704 of a programming unit 108). When more than one calibration table or calibration formula is present, each calibration table or calibration formula may be related to different ranges of values or to different operating conditions or different components or any combination thereof. A calibration formula may be linear or non-linear. A non-linear calibration formula may include quadratic; third-, fourth-, or higher-order polynomial; exponential; logarithmic; or any other suitable terms. A calibration formula may also take the form of a coded routine with heuristic rules or instructions.

In at least some embodiments, the calibration table or calibration formula presents a relationship between measurement values of the light monitor 124 and light output values at the distal portion of the optical lead 122. For example, the calibration table or calibration formula may relate measurements of the light monitor in mA or mV (or other suitable units) to light output at the distal portion of the optical lead in mW (or other suitable units.) In at least some embodiments, the calibration table or the calibration formula presents a relationship between measurement values of the light monitor 124 and values of at least one operational parameter such as, for example, amplitude (e.g., current or voltage amplitude) of the signal driving the light source 120. In at least some embodiments, the calibration table or calibration formula presents a relationship between measurement values of the light monitor 124 and light output values of the light source 120.

The examples of calibration tables and calibration formulas presented in the preceding paragraph utilize one input parameter. It will be understood, however, that other suitable calibration tables and calibration formulas may include multiple input parameters (for example, light output value and amplitude of a signal driving the light source.)

In some embodiments, the calibration table or formula may also incorporate absorption and diffusion coefficients (μa and μd) for the tissues as well as the CSF. For example, the calibration table or formula may estimate a light intensity value received by target tissue after emission from the optical lead and travel through intervening tissue. Preferably, the distance from the emission site on the optical lead to the target tissue site would be known or estimated. This could lead to a patient specific model for dose optimization.

In some embodiments, the calibration table(s) or calibration formula(s) are stored on a memory 105 of a control module 446. The calibration table(s) or calibration formula(s) may be provided to the memory 105 in any suitable manner. For example, the calibration table(s) or calibration formula(s) may be stored on the memory 105 during, or after, manufacture of the control module. As another example, the calibration table(s) or calibration formula(s) may be stored on a memory in the base unit 228 or other portion of the arrangement 200 and downloaded or otherwise provided to, or accessed by, the memory 105 or processor 104 when the arrangement 200 is coupled to the control module 446. As an alternative, the base unit 228 can include an electrical component, such as a resistor, that can be measured to provide a calibration value or an index for selection of a calibration table or calibration formula from a set of calibration tables or calibration formulas. As yet another example, the calibration table(s) or calibration formula(s) may reside on the programming unit 108 or other external device and downloaded or otherwise provided or accessed by the memory 105 or processor 104 through communication with the programming unit or other external device. As a further embodiment, the calibration table(s) or calibration formula(s) may be input by a user (e.g., a clinician, a programmer, or a patient) during a programming or other session. In at least some embodiments, a calibration table or calibration formula may be password protected or otherwise limited to use by authorized individuals.

In some embodiments, the calibration table(s) or calibration formula(s) are stored on a memory 704 of a programming unit 108. The calibration table(s) or calibration formula(s) may be provided to the memory 704 in any suitable manner. For example, the calibration table(s) or calibration formula(s) may be stored on the memory 704 during, or after, manufacture of the programming unit. As another example, the calibration table(s) or calibration formula(s) may be stored on a memory in the control module 446 or base unit 228 or other portion of the arrangement 200 and downloaded or otherwise provided to, or accessed by, the memory 704 of the programming unit. As a further embodiment, the calibration table(s) or calibration formula(s) may be input by a user (e.g., a clinician, a programmer, or a patient) during a programming or other session. In at least some embodiments, a calibration table or calibration formula may be password protected or otherwise limited to use by authorized individuals.

Figures 8, 9:
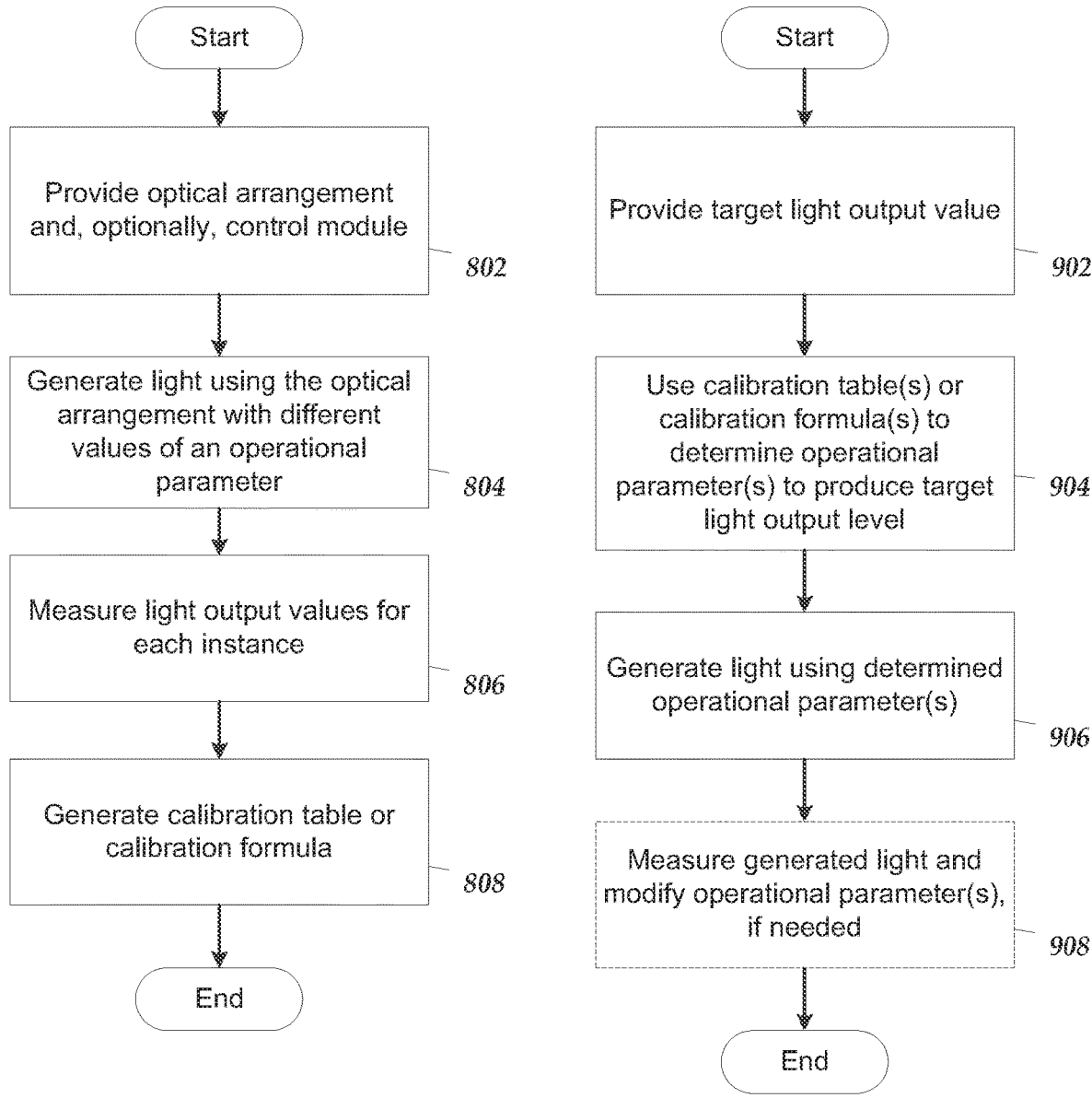
FIG. 8 is a flowchart of one embodiment of a method for generating a calibration table or calibration formula.
FIG. 9 is a flowchart of one embodiment of a method for using a calibration table or calibration formula for an optical stimulation system.

FIG. 8 illustrates one embodiment of a method for generating a calibration table or calibration formula. This method can be performed at any suitable point during the manufacture or subsequent use of the optical stimulation system. For example, the method may be performed after manufacture of the optical arrangement 200 of FIG. 2 at the site of manufacture or elsewhere. As another example, the method may be performed prior to implantation in the patient at the site of implantation or at some site of preparation of the optical stimulation system. In at least some embodiments, the calibration table(s) or calibration formula(s) are not determined until the optical arrangement 200 is associated with a particular control module.

In step 802, an optical arrangement, such as optical arrangement 200 of FIG. 2, is provided. In some embodiments, only the light source 120 or the base unit 228 is provided. In other embodiments, the base unit 228 and the optical lead 122 are provided. In at least some embodiments, a control module is also provided. The control module may be the particular control module that will be implanted with the arrangement 200; in other instances, the control module may be the same type of control module that is intended for use with the arrangement 200; in yet other instances, the control module may be any suitable control module.

In step 804, light is generated using the optical arrangement 200 and different values of an operational parameter (for example, current or voltage amplitude) or for different values of output optical power of the light source 120. In step 806, the light output values are measured for each instance of light that is generated. These light output values may be measured at the output of the optical lead 122 or output of the light source 120 or at any other suitable location. In some embodiments that include a light monitor 124 in the optical arrangement 200, the light output values may be measured using the light monitor. In at least some embodiments, the optical lead 122 or the distal end of the optical lead may be placed in a material that simulates patient tissue to better simulate conditions of use of the lead.

In step 808, the calibration table or calibration formula is generated from the measurements. In at least some embodiments, a calibration table may include entries that are extrapolated or interpolated from the measurements. Any suitable method for obtaining these entries can be used including, but not limited to, nearest-neighbor methods, piece-wise linear methods, spline methods, or other linear or non-linear extrapolation or interpolation methods. Similarly, a calibration formula can be generated by any suitable linear or non-linear extrapolation or interpolation methods. In at least some embodiments, the calibration table or calibration formula will allow for non-linear interpolation or extrapolation.

In at least some embodiments, the calibration table(s) or calibration formula(s) is automatically stored on the base unit 228, control module 446, or programming unit 108, or any combination thereof. In at least some embodiments, a user or device can input the calibration table(s) or calibration formula(s) into the base unit 228, control module 446, or programming unit 108, or any combination thereof FIG. 9 illustrates one embodiment of a method for using calibration table(s) or calibration formula(s). As described above, the calibration table(s) or calibration formula(s) may be stored on the control module, programming unit, or elsewhere. In step 902, a target light output value is provided. The light output value may be for the output of the optical lead 122 or the output of the light source 120 or at any other suitable location. In at least some embodiments, the target light output value is provided by a user, such as a clinician, programmer, or patient. In at least some embodiments, the target light output value may be provided by the system or other device. For example, the system may utilize a feedback loop to modify the output and automatically provide a light output value.

In step 904, the calibration table(s) or calibration formula(s) is used to determine one or more operational parameters (for example, a current or voltage amplitude) to produce the target light output value according to the calibration table(s) or calibration formula(s). In at least some embodiments using a calibration table(s), for light output values that are not provided on the table, linear or non-linear interpolation or extrapolation techniques can be used to determine the operational parameter(s).

In step 906, light is generated using the determined operational parameter(s). In optional step 908, the light output value of the generated light can be measured using, for example, the light monitor 124. If the light output value differs from the target light output value by a threshold amount, the system or user may modify the operational parameter(s). Optionally, step 908 may be performed again to determine whether the actual light output value corresponds, within a threshold amount, to the target output value.

Figure 10:
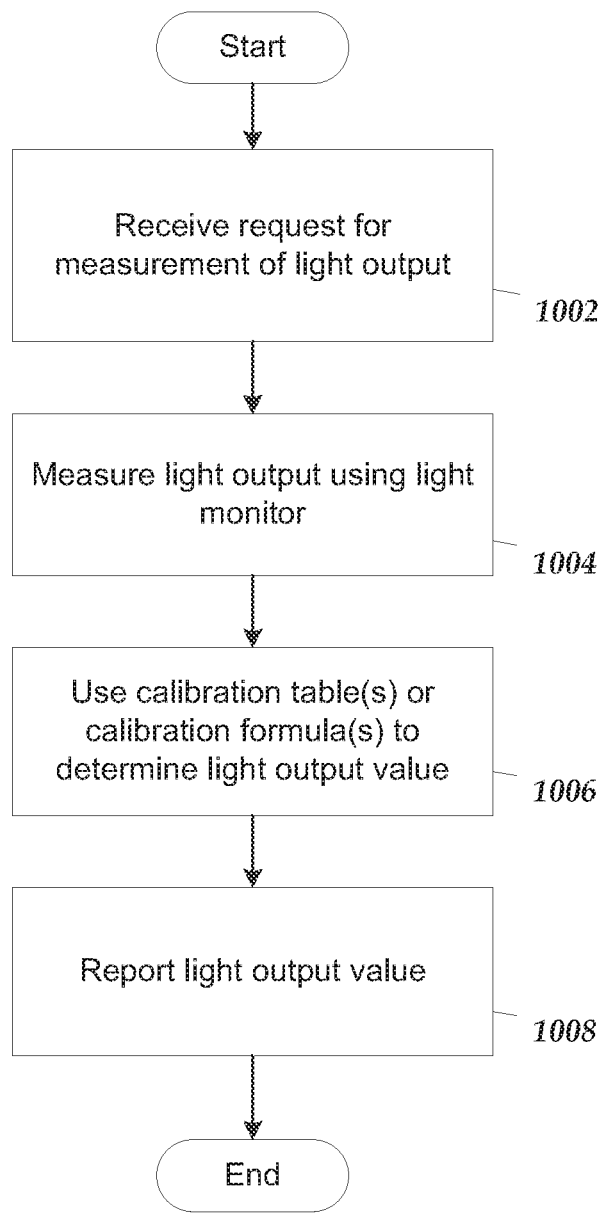
FIG. 10 is a flowchart of one embodiment of another method for using a calibration table or calibration formula for an optical stimulation system.

FIG. 10 illustrates another embodiment of a method for using calibration table(s) or calibration formula(s). As described above, the calibration table(s) or calibration formula(s) may be used to calibrate a measurement of light output (for example, in mA or mV) by the light monitor 124 to a light output value (for example, in mW.) In step 1002, a request for measurement of light output is received. The light output measurement request may be generated by a user (such as a clinician, programmer, or patient) or by the system or other external device or individual.

In step 1004, the light output is measured by the light monitor 124. In step 1006, the calibration table(s) or calibration formula(s) is used to determine the light output value from the light output measured by the light monitor 124. In at least some embodiments using a calibration table(s), for light output measurements that are not provided on the table, linear or non-linear interpolation or extrapolation techniques can be used to determine the light output value. In step 1008, the light output value is reported to the individual or device that made the request.

It will be understood that each block of the flowchart illustrations, and combinations of blocks in the flowchart illustrations and methods disclosed herein, can be implemented by computer program instructions. These program instructions may be provided to a processor to produce a machine, such that the instructions, which execute on the processor, create means for implementing the actions specified in the flowchart block or blocks disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, at least one process may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device.

A system can include one or more processors that can perform the methods (in whole or in part) described above. The methods, systems, and units described herein may be embodied in many different forms and should not be construed as limited to the embodiments set forth herein. Accordingly, the methods, systems, and units described herein may take the form of an entirely hardware embodiment, an entirely software embodiment or an embodiment combining software and hardware aspects. The methods described herein can be performed using any type of processor or any combination of processors where each processor performs at least part of the process. In at least some embodiments, the processor may include more than one processor.

The above specification provides a description of the manufacture and use of the invention. Since many embodiments of the invention can be made without departing from the spirit and scope of the invention, the invention also resides in the claims hereinafter appended.

What is claimed as new and desired to be protected by Letters Patent of the United States is:

1. An implantable optical stimulation system, comprising:
   an implantable light source;
   an implantable optical lead coupled, or coupleable, to the implantable light source;
   at least one of a calibration table or a calibration formula, wherein the at least one of the calibration table or the calibration formula is predetermined and is generated by a calibration procedure specifically using the implantable light source and the implantable optical lead of the implantable optical stimulation system; and
   an implantable control unit coupled, or coupleable, to the implantable light source and comprising
      a memory configured to store the at least one of the calibration table or the calibration formula, and
      a processor coupled to the memory and configured for
         receiving a light intensity value at target tissue after emission from the implantable optical lead and travel through intervening tissue to the target tissue,
         using the at least one of the calibration table or the calibration formula to determine at least one operational parameter for generating the light intensity value at the target tissue, wherein the calibration table or the calibration formula is based, at least in part, on an estimate of the light intensity value at the target tissue, and
         directing the implantable light source, using the at least one operational parameter, to generate light to produce the light intensity value at the target tissue.

2. The implantable optical stimulation system of claim 1, further comprising an implantable light monitor coupled, or coupleable to, the implantable control unit, wherein the implantable optical lead further comprises a first optical waveguide configured to receive light generated by the implantable light source and emit the light from a distal portion of the implantable optical lead and a second optical waveguide configured to receive a portion of the light emitted from the distal portion of the implantable optical lead and direct the received portion of the light to the implantable light monitor.

3. The implantable optical stimulation system of claim 2, wherein the processor is further configured for
   receiving a measurement from the implantable light monitor in response to the generation of light; and
   comparing the measurement to a target light output level to produce the light intensity value at the target tissue.

4. The implantable optical stimulation system of claim 3, wherein the processor is further configured for modifying the at least one operational parameter based on the comparison between the measurement and the target light output level.

5. The implantable optical stimulation system of claim 2, wherein the at least one of the calibration table or the calibration formula comprises a relationship between measurement values of the implantable light monitor and light output values at the distal portion of the implantable optical lead.

6. The implantable optical stimulation system of claim 2, wherein the at least one of the calibration table or the calibration formula comprises a relationship between measurement values of the implantable light monitor and values of the at least one operational parameter.

7. The implantable optical stimulation system of claim 6, wherein the at least one operational parameter is an amplitude of signal provided to the implantable light source to generate the light.

8. The implantable optical stimulation system of claim 1, wherein the at least one of the calibration table or the calibration formula comprises a relationship between light output values at a distal portion of the implantable optical lead and values of the at least one operational parameter.

9. The implantable optical stimulation system of claim 8, wherein the at least one operational parameter is an amplitude of signal provided to the implantable light source to generate the light.

10. A non-transitory processor readable storage media that includes instructions for optical stimulation using an implantable optical stimulation system comprising an implantable light source and an implantable optical lead, wherein execution of the instructions by one or more processor devices of an implantable control unit performs actions, comprising:
    receiving a light intensity value at target tissue after emission from the implantable optical lead and travel through intervening tissue to the target tissue,
    using the at least one of the calibration table or the calibration formula to determine at least one operational parameter for generating the light intensity value at the target tissue, wherein the calibration table or the calibration formula is predetermined and is based, at least in part, on an estimate of the light intensity value at the target tissue, and
    directing the implantable light source, using the at least one operational parameter, to generate light to produce the light intensity value at the target tissue.

11. The non-transitory processor readable storage media of claim 10, wherein the actions further comprise
    receiving a measurement from the implantable light monitor in response to the generation of light; and
    comparing the measurement to a target light output level to produce the light intensity value at the target tissue.

12. The non-transitory processor readable storage media of claim 11, wherein the actions further comprise
    modifying the at least one operational parameter based on the comparison between the measurement and the target light output value.

13. A method of calibrating an implanted optical stimulation system comprising an implanted light source and an implanted optical lead, the method comprising:
    generating light using the implanted light source and different values of an operational parameter;
    measuring a light output value for each of the different values of the operational parameter; and
    generating at least one of a calibration table or a calibration formula for the implanted optical stimulation system using the measured light output values, the different values of the operational parameter, and at least one of a tissue absorption coefficient or a tissue diffusion coefficient.

14. The method of claim 13, wherein the operational parameter is an amplitude of signal provided to the implanted light source to generate the light.

15. The non-transitory processor readable storage media of claim 11, wherein the at least one of the calibration table or the calibration formula comprises a relationship between measurement values of the implantable light monitor and light output values at a distal portion of the implantable optical lead.

16. The non-transitory processor readable storage media of claim 11, wherein the at least one of the calibration table or the calibration formula comprises a relationship between measurement values of the implantable light monitor and values of the at least one operational parameter.

17. The non-transitory processor readable storage media of claim 16, wherein the at least one operational parameter is an amplitude of signal provided to the implantable light source to generate the light.

18. The method of claim 13, wherein the at least one of the calibration table or the calibration formula comprises a relationship between measurement values of an implanted light monitor and light output values at a distal portion of the implanted optical lead.

19. The method of claim 13, wherein the at least one of the calibration table or the calibration formula comprises a relationship between measurement values of an implanted light monitor and values of the at least one operational parameter.

20. The implantable optical stimulation system of claim 2, wherein the at least one of the calibration table or the calibration formula incorporates at least one of a tissue absorption coefficient or a tissue diffusion coefficient.

* * * * *